United States Patent [19]

Eberlin

[11] 3,978,085

[45] Aug. 31, 1976

[54] PROCESS FOR BENZ[f]-2,5-OXAZOCINES

[75] Inventor: John W. Eberlin, Stillwater, Minn.

[73] Assignee: Riker Laboratories, Inc., Northridge, Calif.

[22] Filed: Mar. 7, 1975

[21] Appl. No.: 556,315

[52] U.S. Cl. .............................................. 260/333
[51] Int. Cl.² ....................................... C07D 267/22
[58] Field of Search .................................... 260/333

[56] References Cited
OTHER PUBLICATIONS

Houben–Weyl, vol. 6/4 (1966), pp. 510–518.
Chem. Berichte, vol. 95, No. 5, (1962), pp. 1451, 1454, 1455, 1458, 1459.
Jour. Medicinal and Pharmaceutical Chemistry, vol. 3, No. 1 (1961).
Jour. Am. Chem. Soc., vol. 58 (1936), pp. 2338–2339.
Arzneim.–Forsch., vol. 22, No. 1 (1972), pp. 132–133.

Primary Examiner—Norma S. Milestone
Attorney, Agent, or Firm—Alexander, Sell, Steldt & DeLaHunt

[57] ABSTRACT

An improved process is described for the preparation of 5-lower alkyl-1-phenyl-1,3,4,6-tetrahydro-5H-benz[f]-2,5-oxazocines in which 2-(N-hydroxyethyl-N-lower alkylaminomethyl)-benzhydrols are cyclized in the presence of aqueous hydrogen halide.

9 Claims, No Drawings

PROCESS FOR BENZ[f]-2,5-OXAZOCINES

BACKGROUND OF THE INVENTION

Compounds of the type prepared by the method of the present invention are known, for example see U.S. Pat. No. 3,830,803. These compounds are useful physiologically active substances.

The use of 2-(N-hydroxyethyl-N-lower alkylaminomethyl)-benzhydrols to prepare benz[f]-2,5-oxazocine compounds and use of p-toluene sulfonic acid and of potassium t-butoxide as cyclizing agents in the process for making these compounds have been described (see, for example, Canadian Pat. No. 863,349). However, those methods do not provide high yields of the desired product probably because of the formation of by-products. The mechanism of the cyclization used in the process of the present invention is substantially different from any method for production of those compounds heretofore described. In the present method, the benzhydrol compound is treated with aqueous hydrogen halide, which appears to bring cyclization through replacement of the benzhydrol hydroxy group by halogen and/or formation of a carbonium ion which is followed by cyclization to the desired 8-membered ring.

DETAILED DESCRIPTION OF THE INVENTION

This invention relates to a process which comprises the reaction step

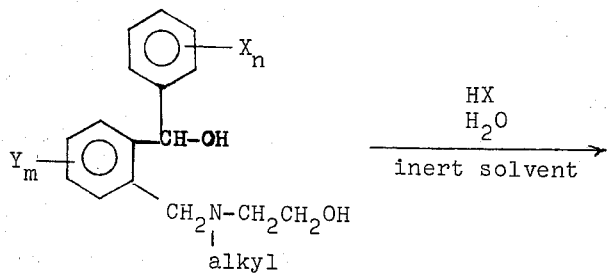 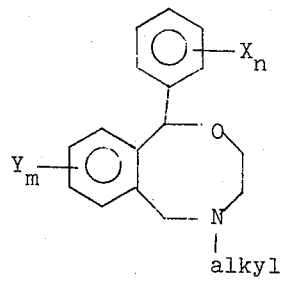

wherein in said formulae alkyl is methyl or ethyl, X is fluorine, chlorine, bromine or methyl, Y is fluorine, chlorine, methyl or methoxy, $n$ is zero, 1 or 2 and $m$ is zero, 1 or 2 and HX is hydrogen chloride, hydrogen bromide or hydrogen iodide. The reaction with aqueous hydrogen halide takes place in an inert solvent, the acidic reaction mixture containing the resulting cyclized product is treated with base to neutralize, the 1-phenylbenzoxazocine product is isolated therefrom as the free base, then converted to a salt.

In this process, high yields of the desired 1-phenylbenzoxazocine are obtained and no significant amounts of undesirable by-products are found. Yields are nearly quantitative.

The hydrogen halides useful in the process of the present invention are hydrogen chloride, hydrogen bromide and hydrogen iodide, and presently preferred is hydrogen bromide. Hydrogen bromide is preferred because when it is used particularly high yields have been obtained.

The starting material benzhydrol is dissolved in a suitable inert solvent such as aliphatic hydrocarbon, for example n-heptane, n-octane and the like, an aromatic hydrocarbon, for example benzene, toluene and the like, or preferably a halogenated hydrocarbon such as dichloromethane, chloroform and the like. Presently preferred are chloroform and toluene. The ratio of solvent to benzhydrol is conveniently about 3 to 1, although this variable is not critical.

The reaction temperature is between about 35°C. and 110°C., although temperature is not critical if efficient reflux is obtained to insure that the concentration of hydrogen halide is maintained. It is not necessary that the reaction be carried out at the reflux temperature of the solvent. Reaction time is not necessarily extended, although reaction times of 1 to 10 hours can be used successfully. The extent of reaction can be monitored by methods known to those skilled in the art, such as chromatography. The reaction is conveniently ended after all starting material has reacted. It will be obvious to those skilled in the art that reaction time will be influenced by reaction temperature, and reaction temperature will be somewhat limited by the solvent used.

The presence of water in the reaction mixture appears to be essential to the success of the reaction.

The ratio of hydrogen halide to benzhydrol compound is also critical. In order to obtain maximum yields of the desired product at least one mole of hydrogen halide per mole of benzhydrol is necessary, and it is presently preferred that at least 1.5 moles of hydrogen halide per mole of benzhydrol is used. Higher concentrations of hydrogen halide reduce the need for longer reaction time and higher reaction temperature and facilitate maintenance of the desired minimum concentration of hydrogen halide; e.g. 5 moles per mole of benzhydrol are useful.

The cyclized free base of the product is obtained by neutralizing the reaction mixture with a base which does not react with the product. A common inorganic base such as sodium hydroxide is generally used. The benzoxazocine is then isolated, conveniently by extraction procedures, then is converted to an acid addition salt, preferably a pharmaceutically acceptable acid addition salt such as the hydrochloride, by reaction with the appropriate acid. Alternatively, the free base is isolated in solution by azeotropic distillation with, e.g., toluene, to remove water, followed by treatment with an acid to form a salt. The acid addition salts are isolated as solids.

The cyclization step proceeds very efficiently and substantially quantitatively; it will therefore be apparent to the art that the limiting procedures as respects recovery of high yields of product are the steps of isolation of the 1-phenylbenzoxazocine base from the reaction mixture and purification to remove acidic or basic reagents and solvents.

The following illustrative examples are provided to show the practice of the method of the invention.

EXAMPLE 1

In a 5 liter flask fitted with a thermometer, a reflux condenser and a stirrer are placed 677.5 g. (2.5 moles) of 2-[N-(2-hydroxy)ethyl-N-methylaminomethyl]-benzhydrol, 1687.5 g. of 48 percent aqueous hydrogen bromide and 2032.5 ml. of chloroform. The mixture is stirred at room temperature (about 23°C.) for about 1 hour, then heated at 55°–60°C. for about 4.5 hours. After cooling to room temperature, 800 g. of 50 percent by weight sodium hydroxide (diluted to 20 percent with water) are added slowly. The organic phase is removed, and the aqueous phase is washed twice with 500 ml. portions of chloroform. The combined organic phases are dried over anhydrous magnesium sulfate, filtered and evaporated to provide 690 g. of 5-methyl-1-phenyl-1,3,4,6-tetrahydro-5H-benz[f]-2,3-oxazocine as an oil.

The oil thus obtained is dissolved in two liters of acetone and treated (with cooling) with gaseous hydrogen chloride until acid to Congo Red. The white solid product is collected by filtration and allowed to dry. The yield of dried 5-methyl-1-phenyl-1,3,4,6-tetrahydro-5H-benz[f]-2,5-oxazocine hydrochloride is 684 g. (94.5 percent, based on starting benzhydrol), m.p. 246°C. Analysis shows better than 99 percent purity.

In another run of the cyclization and isolation steps, 27.1 g. (0.1 mole) of 2-[N-(hydroxy)ethyl-N-methylaminomethyl]benzhydrol are dissolved in 81 ml. of chloroform, and 67.5 g. of 48 percent hydrobromic acid are added with stirring. The reaction mixture is then heated at 55°–60°C. for about 4.5 hours. Thereupon the reaction mixture is cooled in an ice bath and made basic by the slow addition of a mixture of 40 ml. of 10 N-sodium hydroxide solution and 60 ml. of water. The resulting two phase system is separated, and the aqueous layer is extracted once with 30 ml. of chloroform. The combined organic phases are then washed twice with 50 ml. of water, and dried over anhydrous sodium sulfate. Removal of the solid and the solvent leaves an oil, which is dissolved in 70 ml. of acetone, and 10.5 ml. of concentrated hydrochloric acid (36 percent) are added thereto. Crystallization is allowed to proceed at 0°C. for 4 hours. The 5-methyl-1-phenyl-1,3,4,6-tetrahydro-5H-benz[f]-2,3-oxazocine hydrochloride thus produced is collected, washed with 70 ml. of cold acetone and dried in vacuo at 70°C. The yield of salt is 26.0 g., approximately 90 percent.

When the above run is repeated using respectively toluene and dichloroethane instead of chloroform, the hydrochloride salt is obtained in yield of 93.2 percent and 91.4 percent, respectively. It is found that work-up of the reaction mixture using dichloroethane as the solvent is somewhat more troublesome than with the other solvents employed.

Other substituted 1-phenyl-tetrahydrobenzoxazocine compounds which can be prepared using the process of the present invention as set forth in Example 1 are shown in Table I. In each case, the cyclization of the starting compound is effected by means of treatment with aqueous hydrobromic acid and isolation of the product is by extraction and formation of the hydrochloride salt.

TABLE I

| Ex. No. | Starting Material | Product |
|---|---|---|
| 2 | 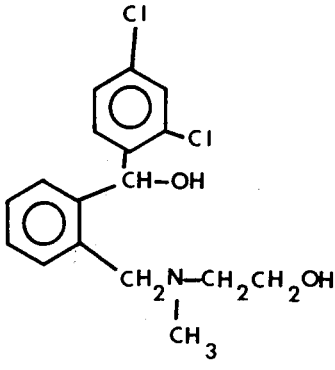 | 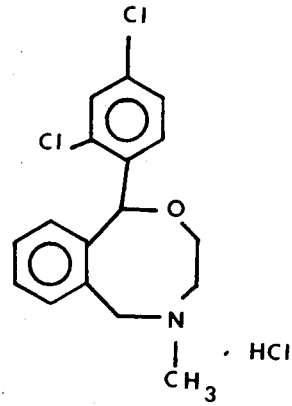 |
| 3 | 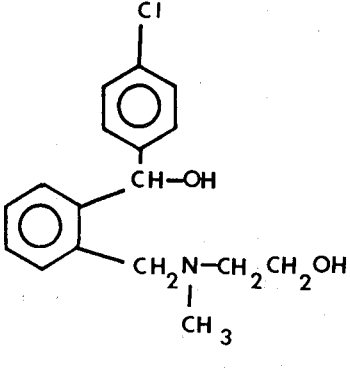 | 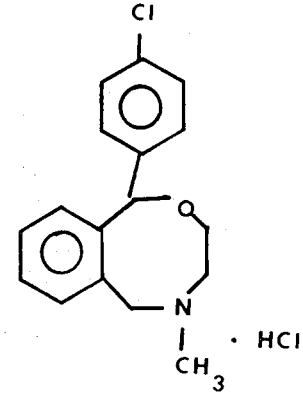 |

TABLE 1 (continued)
| | Starting Material | Product |
|---|---|---|
| 4 | 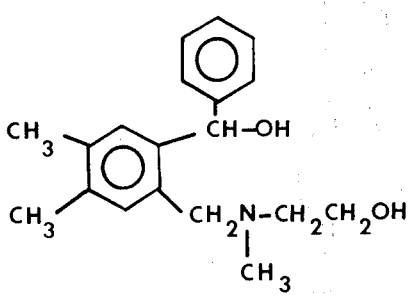 | 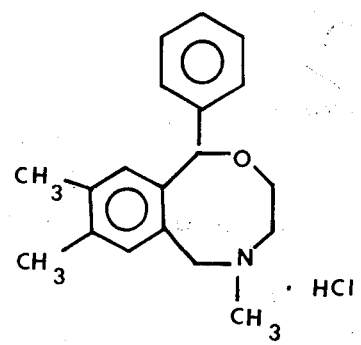 |
| 5 | 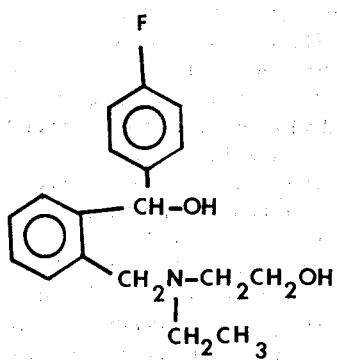 | 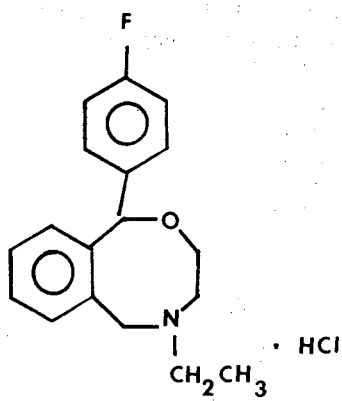 |
| 6 | 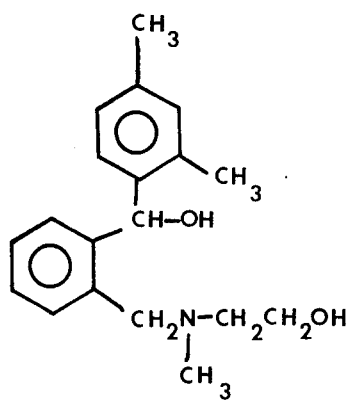 | 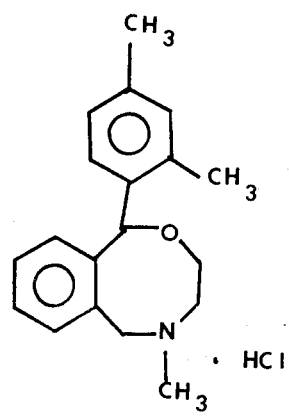 |
| 7 | 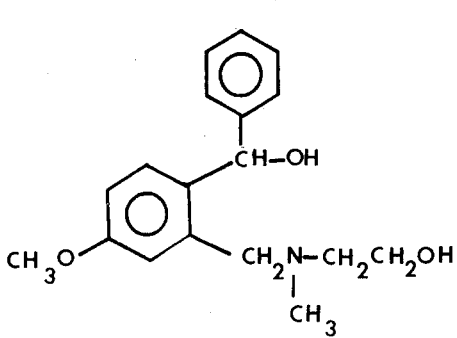 | 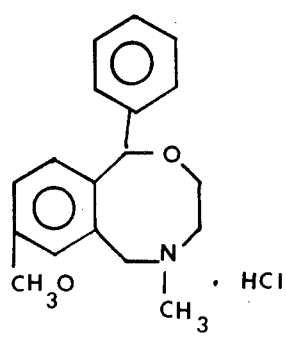 |

TABLE I (continued)

| Starting Material | Product |
|---|---|
| 8 | (structure with F, CH-OH, phenyl, CH₂N(CH₃)-CH₂CH₂OH) | (benzoxazocine structure with F, phenyl, N-CH₃ · HCl) |

What is claimed is:

1. In a process for producing 1-phenyl-1,3,4,6-tetrahydrobenzoxazocines the step which comprises treating a compound of the formula

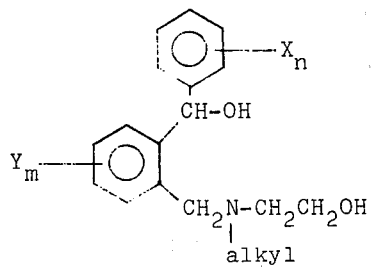

wherein alkyl is methyl or ethyl, X is fluorine, chlorine, bromine or methyl, Y is fluorine, chlorine, methyl or methoxy, n is zero, 1 or 2 and m is zero, 1 or 2 with at least an equimolar amount of aqueous hydrogen bromide in an inert solvent.

2. The process which comprises the step of claim 1 followed by treating the acidic reaction mixture with base to neutralize, isolating the free 1-phenyl-1,3,4,6-tetrahydrobenzoxazocine, and converting the said base to an acid addition salt.

3. The process of claim 1 wherein the solvent is dichloromethane or chloroform.

4. The process of claim 1 wherein alkyl is methyl.

5. The process of claim 4 wherein n is zero.

6. The process of claim 5 wherein m is zero.

7. The process of claim 5 wherein X is chlorine.

8. The process of claim 2 wherein the salt is a hydrochloride.

9. The process of claim 2 wherein the solvent is toluene.

* * * * *